United States Patent
Dirauf et al.

(10) Patent No.: US 9,541,486 B2
(45) Date of Patent: Jan. 10, 2017

(54) PANEL WITH STRAIN GAUGES FOR MEASURING DEFORMATION INFORMATION

(71) Applicants: Franz Dirauf, Ebensfeld (DE); Kerstin Farmbauer, Pressath (DE)

(72) Inventors: Franz Dirauf, Ebensfeld (DE); Kerstin Farmbauer, Pressath (DE)

(73) Assignee: Siemens Aktiengesellschaft, München (DE)

( * ) Notice: Subject to any disclaimer, the term of this patent is extended or adjusted under 35 U.S.C. 154(b) by 60 days.

(21) Appl. No.: 14/323,351

(22) Filed: Jul. 3, 2014

(65) Prior Publication Data

US 2015/0007664 A1  Jan. 8, 2015

(30) Foreign Application Priority Data

Jul. 5, 2013 (DE) .................. 10 2013 213 219

(51) Int. Cl.
| | |
|---|---|
| G01B 7/16 | (2006.01) |
| G01N 3/20 | (2006.01) |
| G01L 7/08 | (2006.01) |
| G01L 1/20 | (2006.01) |
| G01L 1/22 | (2006.01) |
| A61B 6/04 | (2006.01) |
| A61B 6/00 | (2006.01) |

(52) U.S. Cl.
CPC .............. *G01N 3/20* (2013.01); *A61B 6/0407* (2013.01); *A61B 6/5276* (2013.01); *G01L 1/205* (2013.01); *G01L 1/2206* (2013.01); *G01L 7/08* (2013.01)

(58) Field of Classification Search
CPC .............. A61G 7/00; A61B 6/00; G01L 1/20; G01L 1/22; G06F 3/044
USPC .......................................................... 73/763
See application file for complete search history.

(56) References Cited

U.S. PATENT DOCUMENTS

| | | | |
|---|---|---|---|
| 2,508,456 A | 5/1950 | Gustafsson | |
| 5,528,151 A | 6/1996 | Perez | |
| 7,454,987 B2 | 11/2008 | Reger | |
| 7,505,803 B2* | 3/2009 | Boese | A61B 5/103 |
| | | | 5/601 |
| 8,210,055 B2 | 7/2012 | Klein et al. | |
| 8,984,685 B2* | 3/2015 | Robertson | A61G 7/018 |
| | | | 5/611 |

(Continued)

FOREIGN PATENT DOCUMENTS

| | | |
|---|---|---|
| CN | 101484787 A | 7/2009 |
| CN | 101965505 A | 2/2011 |

(Continued)

OTHER PUBLICATIONS

German Office Action dated Jan. 16, 2014 in corresponding German Patent Application No. DE 10 2013 213 219.0 with English translation.

(Continued)

*Primary Examiner* — Lisa Caputo
*Assistant Examiner* — Octavia Hollington
(74) *Attorney, Agent, or Firm* — Lempia Summerfield Katz LLC

(57) ABSTRACT

A panel includes a plurality of integrated strain gauges for measuring deformation information relating to the panel. The strain gauges are arranged parallel to one another in the longitudinal direction of the panel and have at least two different lengths.

14 Claims, 3 Drawing Sheets

(56) References Cited

U.S. PATENT DOCUMENTS

| | | | |
|---|---|---|---|
| 2003/0136201 A1 | 7/2003 | Hubbard, Jr. | |
| 2008/0072683 A1 | 3/2008 | Liu et al. | |
| 2008/0289106 A1 | 11/2008 | Beyer et al. | |
| 2011/0296613 A1 | 12/2011 | Farmbauer et al. | |
| 2015/0230748 A1* | 8/2015 | Marcandelli | A61B 5/4519 600/587 |

FOREIGN PATENT DOCUMENTS

| | | |
|---|---|---|
| DE | 102004008432 | 9/2005 |
| DE | 102004041897 | 3/2006 |
| DE | 102007023919 | 11/2008 |
| DE | 102010023033 | 12/2011 |
| EP | 1994959 A1 | 11/2008 |
| GB | 654736 A | 6/1951 |

OTHER PUBLICATIONS

Chinese office Action for related Chinese Application No. 201410315686.3 dated Oct. 9, 2016 with English Translation.

* cited by examiner

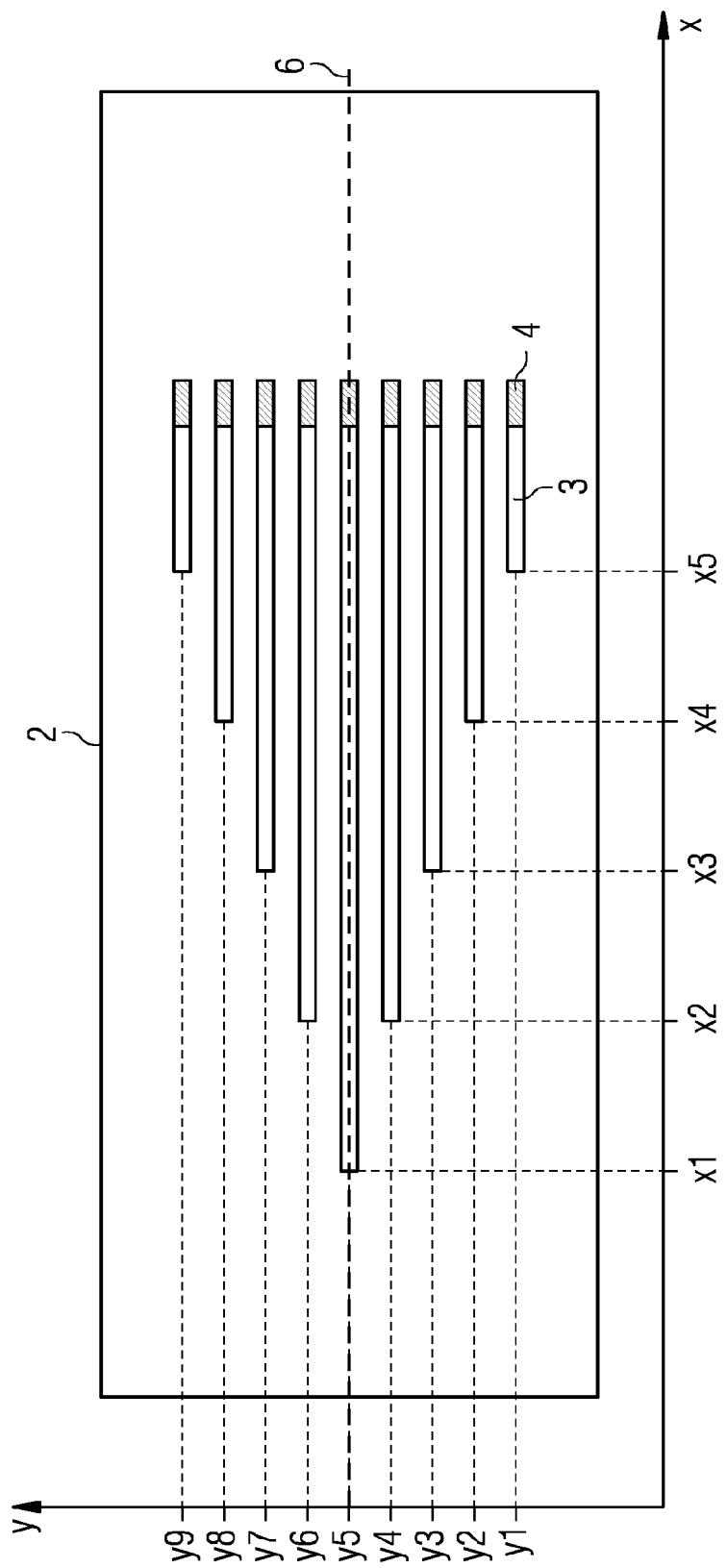

PANEL WITH STRAIN GAUGES FOR MEASURING DEFORMATION INFORMATION

This application claims the benefit of DE 102013213219.0, filed on Jul. 5, 2013, which is hereby incorporated by reference in its entirety.

BACKGROUND

The disclosed embodiments relate to a panel, such as a couch panel for supporting a patient, with a plurality of integrated strain gauges for measuring deformation information relating to the panel.

Strain gauges are used for registering extensions or compressions of deformation bodies. By way of example, DE 102004008432 A1 describes extension measuring fibers or fiber strands. The extension measuring fibers are made of carbon fibers (CFRP) provided with metallic sleeves at the ends thereof. The sleeves assume a contacting function and are, for this purpose, attached to the extension measuring fibers via an electrically conductive adhesive or a mechanical clamping connection. The sleeves are employed as solder connections for connecting lines that connect the strain gauges in electric circuits with the power supply and amplifier elements. The strain gauges are made of electrically conductive measurement fibers and change the electric resistance value thereof depending on extension. The strain gauges may be used in measurement circuits, for example, in Wheatstone measurement circuits, and may be used for precise evaluation of extension-dependent measurement variables. The measuring fibers have high breaking strength and a high fatigue-proof extension capability of at least 1.2%.

DE 102004041897 A1 describes a strain gauge used for establishing bending of a tabletop, which is used for patient support in the case of treatment or diagnosis. The sag of the tabletop may be calculated as a function of the extension measured by the gauge.

DE 102010023033 A1 discloses that strain gauges at a plurality of points along the length of a couch panel may be used to establish the deflection line of the couch panel.

When integrating strain gauges into a panel, information may be established only to a restricted extent due to the dimensions of the strain gauges and of the panel, and due to the electronic connections used to evaluate the resistance change of the strain gauges.

There is a need for an intelligent arrangement of strain gauges in a panel such that various items of useful information may be obtained.

SUMMARY AND DESCRIPTION

The scope of the present invention is defined solely by the appended claims and is not affected to any degree by the statements within this summary.

The present embodiments may obviate one or more of the drawbacks or limitations in the related art. For example, the disclosed embodiments may provide a panel with a plurality of integrated strain gauges for measuring deformation information relating to the panel.

According to one embodiment, the strain gauges are arranged parallel to one another in the longitudinal direction of the panel. In this case, the strain gauges have at least two different lengths (e.g., a multiplicity of different lengths). In this case, measurement strips are configured such that the measurement strips have a significantly greater extent (e.g., by one order of magnitude) in one direction (referred to herein as the longitudinal direction) than in the other directions (transverse direction and thickness as referenced herein).

The panel has a longitudinal direction or longitudinal extent, a transverse direction or transverse extent, and a thickness. The thickness is significantly smaller (e.g., at least one order of magnitude in medical applications) than the dimensions in the other directions. The longitudinal extent of the panel may be greater than the transverse extent; however, a square panel may be provided. The strain gauges are arranged in the longitudinal direction of the panel, e.g., parallel to the longitudinal direction (and parallel to one another). The plurality of mutually parallel strain gauges in the longitudinal direction may optionally be complemented by further measurement strips or by a further plurality of parallel measurement strips, which are integrated in the panel.

A relatively large number of measurement strips may be arranged as a result of the parallel arrangement of measurement strips of different lengths. Each relatively large measurement strip supplies different information such that comparatively much information is available compared to the prior art for a precise calculation of the panel sag or panel deformation.

In accordance with one embodiment, one pair of strain gauges (of equal length) extends symmetrically with respect to the centerline in the longitudinal direction of the panel. The pair of strain gauges is provided in each case for a plurality of different strain gauge lengths per unit length. A symmetric pair of strain gauges is not necessary for all strain gauge lengths. By way of example, a strain gauge may be provided on the centerline in the longitudinal direction. The strain gauge may not have a counterpart in terms of length.

Via pairs of symmetrically arranged strain gauges, two items of information may be established for different positions with respect to the transverse direction of the panel for one strip length or one panel position. Therefore, information is also established with respect to a deformation of the panel relating to the transverse direction. By way of example, a positioning of a load (e.g., of a patient) on the panel may be established and quantified. The positioning may be asymmetric with respect to the centerline in the longitudinal direction.

In accordance with one configuration, the lengths of the strain gauges increase monotonically or strictly monotonically with decreasing distance from the centerline. By way of example, the deformation information may be established because connection elements for measuring the electric resistance of the respective strain gauge are arranged at the ends of the strain gauges.

The disclosed embodiments also relate to a device for determining deformation information for a panel as described herein and to which a load has been applied. The device is configured for establishing at least one item of deformation information caused by the load in the transverse direction of the panel by comparing extension information determined by pairs of strain gauges of equal length. The pairs of strain gauges are symmetric with respect to the centerline in the longitudinal direction. This device may also be configured to establish at least one item of deformation information, caused by the load, in the longitudinal direction of the panel.

BRIEF DESCRIPTION OF THE DRAWINGS

FIG. 3 shows another exemplary panel with integrated measurement strips in accordance with one embodiment.

DETAILED DESCRIPTION

Figure 1A:
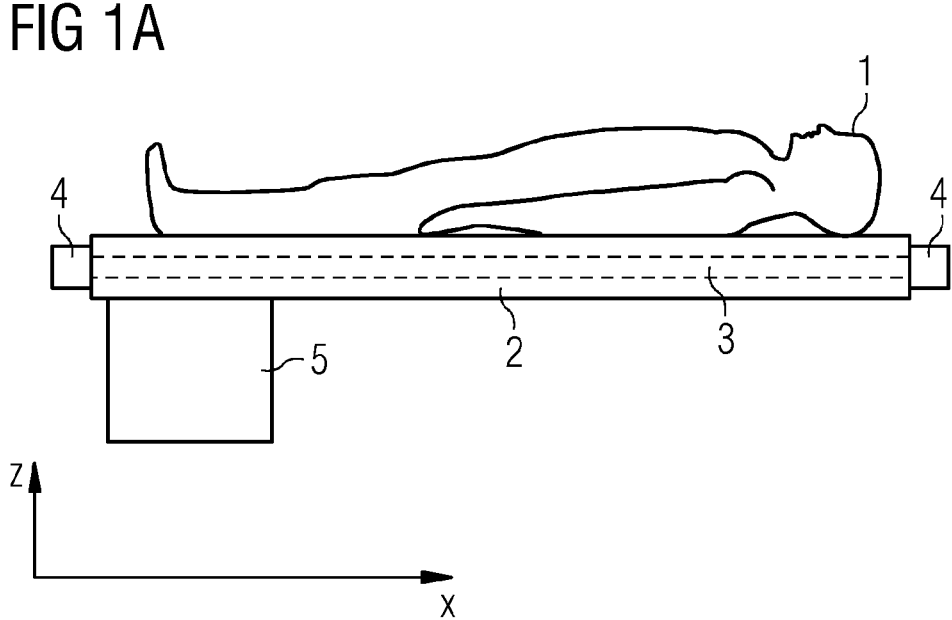
FIGS. 1A and 1B illustrate an example of measuring a couch panel deformation by a load.
Figure 1B:
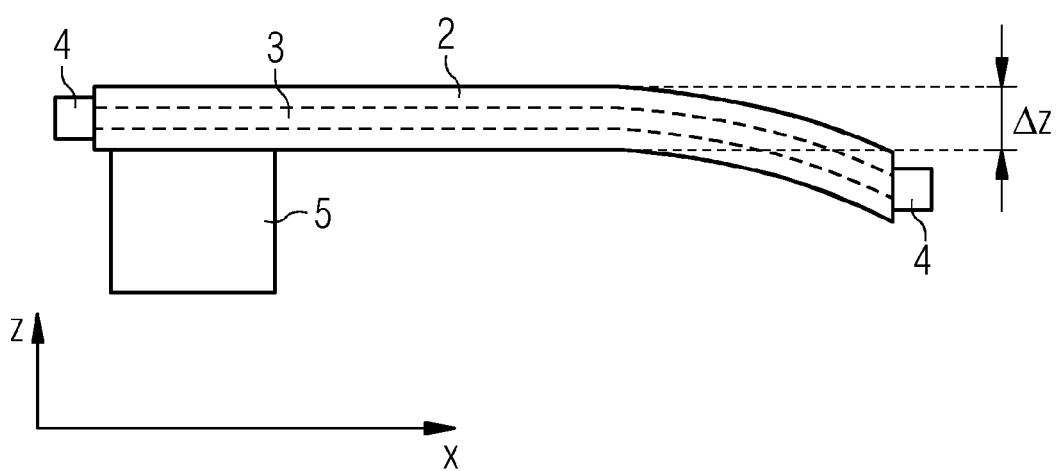

FIGS. 1A and 1B show a side view of a patient support device with an integrated strain gauge. A tabletop 2 (panel, patient couch) is depicted, on which a patient 1 may be supported for purposes of a medical examination. The material of the tabletop 2 is configured in accordance with the examination technique to be used. A measurement strip 3 is integrated into the tabletop 2. The measurement strip extends along the longitudinal direction of the tabletop 2. The longitudinal direction of the tabletop is denoted by the x-axis of a coordinate system and the direction perpendicular to the tabletop is denoted by the z-axis of the coordinate system. There is a sag $\Delta z$ of the tabletop 2 as a result of the weight of the patient 1, as depicted in FIG. 1B. The measurement strip 3 integrated into the tabletop 2 in the x-direction extends when the tabletop sags. Here, the change in length of the measurement strip 3 is proportional to the sag $\Delta z$ of the tabletop 2. As the tabletop 2 sags further, there also is a greater change in length of the measurement strip 3.

The measurement strip 3 consists of a thin wire or of a different stretchable electrically conductive material, e.g., carbon fibers. Sensors 4 are attached to the ends of the measurement strip 3. These sensors 4 measure electric resistance of the measurement strip 3. Because the electric resistance of the measurement strip 3 changes with the length of the measurement strip 3, the change in the electric resistance, the change in length and, as a result thereof, the sag $\Delta z$ of the tabletop 2 may be established via the sensors 4.

For precisely registering the deformation of the tabletop, the overall sag $\Delta z$ of the tabletop 2 is established, and more precise information relating to the deflection line is obtained. The information may be different in different examinations even if the overall sag is the same, for example, in the case of different positions of the patient's center of gravity.

Figure 2:
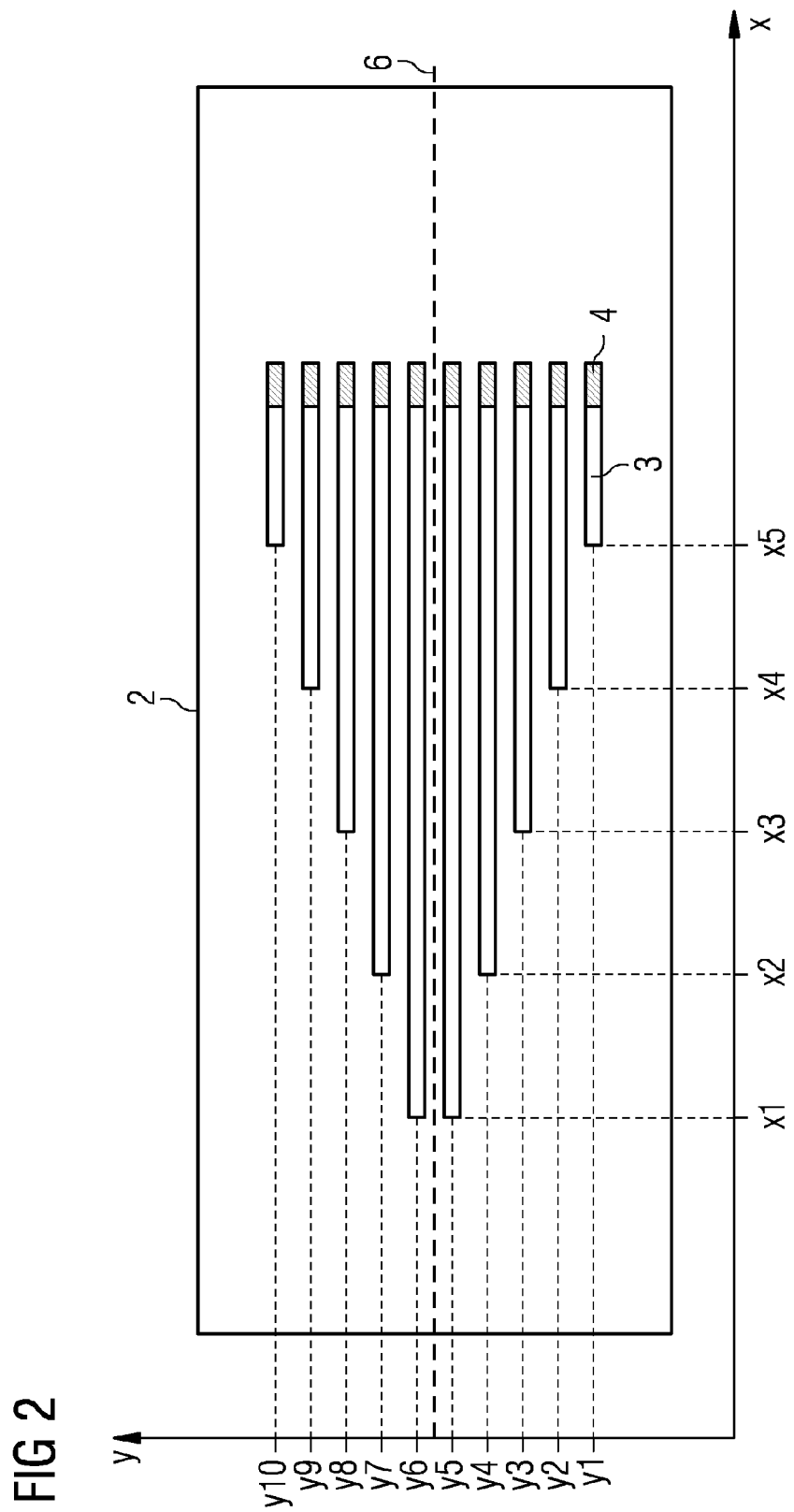
FIG. 2 shows an exemplary panel with integrated measurement strips in accordance with one embodiment.

FIG. 2 shows a couch panel 2 according to one embodiment. The couch panel 2 is provided with a multiplicity of strain gauges 3. On the ends of the strain gauges 3, each strain gauge 3 has connection elements 4 for measuring the electric resistance of the respective strain gauge. The strain gauges have different lengths, which are characterized by the endpoints on the x-axis $x_1 \ldots x_5$. For each of these lengths characterized by the x-values, there is one pair of strain gauges arranged symmetrically with respect to the centerline 6 in the longitudinal direction. This arrangement leads to a doubling of the strain gauges 3 to a number of 10 strain gauges with five different lengths. The individual strain gauges correspond to different values $y_1 \ldots y_{10}$ in the transverse direction.

Using this information, the stretching behavior may be determined both in the longitudinal direction (or x-direction) and in the transverse direction (or y-direction). If $M(i,j)$ is the measurement strip characterized by the endpoint $(x_i, y_j$: $i \in \{1 \ldots 5\}$, $j \in \{1 \ldots 10\})$ and if $\Delta z(M(i,j))$ is the corresponding measurement strip sag, then, for $i \in \{1 \ldots 5\}$, then $(\Delta z(M(i,6-i))+\Delta z(M(i,5+i)))/2$ is a measure of the (averaged) longitudinal sag at the point $x_i$ and $(\Delta z(M(i,6-i))-\Delta z(M(i,5+i)))/(Y_{6-i}-y_{5+i})$ is a measure of the transverse sag in the transverse direction defined by $x_i$. Formula-based approaches for a deflection line are described in, e.g., DE 102007023919 DE. The parameters of the approach may be determined by, e.g., fitting to the data above.

FIG. 3 shows another exemplary embodiment with a strain gauge centrally disposed with respect to the longitudinal direction.

On the basis of measurement data from the above-described sensor arrangement, which is realized with strain gauges, the following information, inter alia, may be calculated and derived with the aid of modeling.

Trajectory Correction:

On the basis of the established deflection line, the position or the movement trajectory of an emitter or detector system, or of another component, may be corrected such that the desired distance from the patient or from the table top is set automatically as if the tabletop were not sagging. Thus, there is calculated compensation of the sag.

Determining Patient Load, Position and Orientation:

On the basis of the established deflection line, the position of the center of gravity of the load may approximately be established or verified in addition to the weight of the patient. As a result the position of the patient on the tabletop may be approximately established or verified. DE 102007023919 DE, cited above, describes the bending line as a function of the following two parameters: center of gravity of the patient and weight of the patient, which may be obtained by fitting the bending line to the measured values. The orientation in which the patient lies on the table top (location of head and feet) may be identified from the position of the center of gravity of the load.

Identification and Warning Signal in the Case of Overloading:

Based on the established bending line, when the tabletop is loaded beyond the permitted limits may be derived or identified. In this case, a warning signal may be emitted and suitable reactions in the control of the system may be triggered (e.g., applying the brakes, adapting the speed). The incident may then be recorded automatically in the log file of the control for diagnostic and maintenance purposes.

Identification of Improper Use:

By way of example, improper use of the tabletop includes the application of a great load on the outer, unsupported end of the tabletop (at a distance from the foot of the table). By way of example, this load application occurs if persons sit down on the end of the table. Based on the profile of the established bending line, such improper use may be identified, and a warning may be emitted. The result may likewise be stored in the log file and evaluated with regard to damage to the tabletop.

Collision Identification:

From the dynamic change of the established bending line, collision between the tabletop and another object (e.g. patient wheelchair) may be identified. Suitable protective measures may be adopted, such as e.g. stopping motorized movements.

Checking the Integrity and Service Life:

A characteristic bending line emerges for the tabletop when applying defined loads to predetermined positions. Both in the manufacturing process and also, subsequently, in clinical use, this quick and easy-to-perform test may be used to check as to whether there is damage to, or aging (change in the bending properties as a result of material fatigue) of, the tabletop.

Establishing the Load Spectrum During Clinical Use:

By recording the measured bending lines during clinical operation, statistical criteria may be obtained for designing mechanical and electronic components, and also for service life prediction of composites and appropriate servicing (predictive maintenance).

The disclosed embodiments are not restricted to the cases described in the exemplary embodiments. By way of example, the measurement strip configuration shown in FIG. 2 and FIG. 3 may be repeated a number of times along a panel. The measurement strip configuration may also occur in a mirrored form. By way of example, a couch panel with two measurement strip configurations may be configured as in FIG. 2, in which the second configuration is mirrored relative to the other one in view of the transverse direction. Further embodiments emerge to a person skilled in the art by purely routine measures and relate to the subject matter of the present application for which protection is sought.

Moreover, use is not restricted to medical technology. The application is conceivable in all cases where deformation or bending plays a role. For example, the disclosed embodiments may be used in distant fields of application, such as the testing of the deformation of diving boards for swimming pools.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it should be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A panel comprising:
a plurality of integrated strain gauges configured to measure deformation information relating to the panel, the plurality of integrated strain gauges having a plurality of pairs of strain gauges,
wherein the strain gauges are arranged parallel to one another and extend in a longitudinal direction of the panel,
wherein each pair of strain gauges include equal length strain gauges symmetrically arranged on opposite sides of a centerline of the panel,
wherein each pair of strain gauges has a different length from each other pair of strain gauges, and
wherein the lengths of the plurality of strain gages increase with decreasing distance from the centerline.

2. The panel of claim 1,
wherein one length of the plurality of different strain gauge lengths is provided by one strain gauge of the plurality of strain gauges arranged on the centerline and the pairs of strain gauges provide all of the other strain gauge lengths of the plurality of strain gauge lengths.

3. The panel of claim 2, wherein each strain gauge of the plurality of strain gauges comprises:
connection elements configured to measure electric resistance of the respective strain gauge and arranged at ends of the respective strain gauge.

4. The panel of claim 2, wherein the panel is a couch panel for supporting a patient.

5. The panel of claim 1, wherein each strain gauge of the plurality of strain gauges comprises:
connection elements configured to measure electric resistance of the respective strain gauge and arranged at ends of the respective strain gauge.

6. The panel of claim 5, wherein the panel is a couch panel for supporting a patient.

7. The panel of claim 1, wherein the panel is a couch panel for supporting a patient.

8. The panel of claim 1, wherein the panel includes no strain gauges extending in a transverse direction, perpendicular to the longitudinal direction.

9. A device for determining deformation information for a panel to which a load is applied, the device comprising:
a plurality of integrated strain gauges for measuring deformation information relating to the panel,
wherein the strain gauges are arranged parallel to one another with respect to a longitudinal direction of the panel, and wherein the strain gauges have at least two different lengths;
wherein pairs of the plurality of strain gauges extend symmetrically in the longitudinal direction with respect to a centerline of the panel, and wherein the strain gauges of each pair are equal length strain gauges symmetrically arranged on opposite sides of a centerline of the panel;
wherein the device is configured to establish at least one item of deformation information for deformation caused by the load in a transverse direction of the panel based on a comparison of extension information determined by the pairs of the plurality of strain gauges.

10. The device as claimed in claim 9, wherein the device is further configured to establish at least one item of deformation information for deformation caused by the load in the longitudinal direction of the panel.

11. A panel integrated with a plurality of strain gauges comprising:
a centerline strain gauge arranged along a centerline of the panel in a longitudinal direction of the panel;
at least one pair of strain gauges, each strain gauge of each pair of the at least one pair of strain gauges being arranged in parallel on opposite sides of the centerline and symmetric in the longitudinal direction with respect to the centerline of the panel, wherein the strain gauges of the at least one pair of strain gauges are parallel, and
wherein the centerline strain gauge and the at least one pair of strain gauges have at least two different lengths;
wherein a longitudinal length of the plurality of strain gauges is at least one order of magnitude greater than a transverse length of the plurality of strain gauges and at least one order of magnitude greater than a thickness value of the plurality of strain gauges.

12. The panel of claim 11, wherein a longitudinal length of each pair of the at least one pair of strain gauges increases with decreasing distance from the centerline.

13. The panel of claim 11, wherein each strain gauge of the plurality of strain gauges further comprises:
connection elements configured to measure electric resistance of the respective strain gauge and arranged at ends of the respective strain gauge.

14. The panel of claim 11, wherein the panel is a couch panel for supporting a patient.

\* \* \* \* \*